United States Patent
Zhang et al.

(10) Patent No.: US 12,012,614 B2
(45) Date of Patent: Jun. 18, 2024

(54) INDUCER FOR INDUCING A MESENCHYMAL STEM CELL TO DIFFERENTIATE INTO AN ISLET CELL

(71) Applicant: QINGDAO RESTORE BIOTECHNOLOGY CO., LTD., Qingdao (CN)

(72) Inventors: Bingqiang Zhang, Qingdao (CN); Mengmeng Chen, Qingdao (CN); Cuicui Li, Qingdao (CN); Erpu Wang, Qingdao (CN); Fubin Wang, Qingdao (CN); Wei Zou, Qingdao (CN); Xueqi Fu, Qingdao (CN); Cuijuan Liu, Qingdao (CN)

(73) Assignee: QINGDAO RESTORE BIOTECHNOLOGY CO., LTD., Qingdao (CN)

( * ) Notice: Subject to any disclaimer, the term of this patent is extended or adjusted under 35 U.S.C. 154(b) by 779 days.

(21) Appl. No.: 17/259,462

(22) PCT Filed: May 25, 2020

(86) PCT No.: PCT/CN2020/092082
§ 371 (c)(1),
(2) Date: Jan. 11, 2021

(87) PCT Pub. No.: WO2021/143001
PCT Pub. Date: Jul. 22, 2021

(65) Prior Publication Data
US 2021/0363489 A1 Nov. 25, 2021

(30) Foreign Application Priority Data
Jan. 13, 2020 (CN) .......................... 202010032047.1

(51) Int. Cl.
*C12N 5/071* (2010.01)

(52) U.S. Cl.
CPC ........ *C12N 5/0676* (2013.01); *C12N 2501/14* (2013.01); *C12N 2501/165* (2013.01); *C12N 2501/335* (2013.01); *C12N 2501/37* (2013.01); *C12N 2501/999* (2013.01)

(58) Field of Classification Search
CPC .............. C12N 5/0676; C12N 2501/14; C12N 2501/165; C12N 2501/335; C12N 2501/37; C12N 2501/999
See application file for complete search history.

(56) References Cited

FOREIGN PATENT DOCUMENTS

| CN | 103756954 A | 4/2014 |
|----|-------------|--------|
| CN | 104845932 A | 8/2015 |
| CN | 105132369 A | 12/2015 |
| CN | 106190965 A | 12/2016 |
| CN | 107372464 A | 11/2017 |
| KR | 20160022757 A | 3/2016 |

OTHER PUBLICATIONS

Pittenger, M. F., et al., "Mesenchymal stem cell perspective: cell biology to clinical progress," NPJ Regen Med 4: 22. doi: 10.1038/s41536-019-0083-6. (Year: 2019).*
Dayem, A. A., et al., "Production of Mesenchymal Stem Cells Through Stem Cell Reprogramming," Int J Mol Sci 20(8): 1922. doi: 10.3390/ijms20081922. (Year: 2019).*
Costa, L. A., et al., "Functional heterogeneity of mesenchymal stem cells from natural niches to culture conditions: implications for further clinical uses," Cell Mol Life Sci 78: 447-467. doi: 10.1007/s00018-020-03600-0. (Year: 2020).*
Viswanathan, S., et al., "Mesenchymal stem versus stromal cells: International Society for Cell & Gene Therapy (ISCT®) Mesenchymal Stromal Cell committee position statement on nomenclature," Cytotherapy 21(10):1019-1024. doi: 10.1016/j.jcyt.2019.08.002. (Year: 2019).*
Egholm, C., et al., "GLP-1 inhibits VEGFA-mediated signaling in isolated human endothelial cells and VEGFA-induced dilation of rat mesenteric arteries," Am J Physiol Heart Circ Physiol 311(5): H1214-H1224. doi: 10.1152/ajpheart.00316.2016. (Year: 2016).*
Chen, T., et al., "Parathyroid hormone and its related peptides in bone metabolism," Biochem Pharmacol 192:114669. doi: 10.1016/j.bcp.2021.114669. (Year: 2021).*
Sehgal, S. N., Sirolimus: its discovery, biological properties, and mechanism of action, Transplant Proc 35(3 Suppl): 7S-14S. doi: 10.1016/s0041-1345(03)00211-2. (Year: 2003).*
Sayedi, Z., et al., "Icariin: A Promising Natural Product in Biomedicine and Tissue Engineering," J Funct Biomater 14(1):44. doi: 10.3390/jfb14010044. (Year: 2023).*
Ryu, M. S., et al., "Zinc transporters ZnT1 (Slc30a1), Zip8 (Slc39a8), and Zip10 (Slc39a10) in mouse red blood cells are differentially regulated during erythroid development and by dietary zinc deficiency," J Nutr 138 (11): 2076-83. doi: 10.3945/jn.108.093575. (Year: 2008).*
Apte, R. S., et al., "VEGF in Signaling and Disease: Beyond Discovery and Development," Cell 176(6):1248-1264. doi: 10.1016/j.cell.2019.01.021. (Year: 2019).*
Tayaramma, T., et al. "Chromatin-remodeling factors allow differentiation of bone marrow cells into insulin-producing cells," Stem Cells 24(12): 2858-2867. doi: 10.1634/stemcells.2006-0109. (Year: 2006).*
Gabr, M., et al., "From Human Mesenchymal Stem Cells to Insulin-Producing Cells: Comparison between Bone Marrow- and Adipose Tissue-Derived Cells," Biomed Res Int. 2017: 2017:3854232. (Year: 2017).*

(Continued)

*Primary Examiner* — Tracy Vivlemore
*Assistant Examiner* — Eric J Rogers
(74) *Attorney, Agent, or Firm* — Zhigang Ma

(57) ABSTRACT

The present invention belongs to the field of biomedicine, and relates to an inducer for inducing a mesenchymal stem cell to differentiate into an islet cell. An inducer for inducing a mesenchymal stem cell to differentiate into an islet cell consisted of the following components: GLP-1, parathyroid hormone, paracetamol, rapamycin, icariin, trametinib, EPO and VEGF. Each component in a inducer for inducing a mesenchymal stem cell to differentiate into an islet cell of the present invention is safe and non-toxic, requiring fewer steps and short time to induce differentiation, with high induction efficiency.

3 Claims, 1 Drawing Sheet

(56) References Cited

OTHER PUBLICATIONS

Internation Search Report and Written Opinion issued in corresponding International application No. PCT/CN2020/092082 with a completion date of Sep. 2, 2020 (9 pages).
Jia; "Differentiation Of Human Bone M~'Row Mesenchymal Stem Cells(Hbmscs)Into Insulin-Secreting Cells;" Chin J Diabetes, Jul. 2009, vol. 17, No. 7, pp. 505-509 ( ).
El-Asfar; "Obestatin Can Potentially Differentiate Wharton's Jelly Mesenchymal Stem Cells Into Insulin-Producing Cells;", Cell Tissue Res 372 (1) : 91-98 (2017).

* cited by examiner

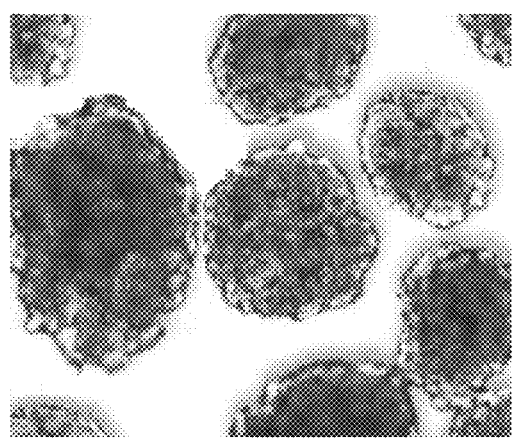

INDUCER FOR INDUCING A MESENCHYMAL STEM CELL TO DIFFERENTIATE INTO AN ISLET CELL

TECHNICAL FIELD

The present invention belongs to the field of biomedicine, and relates to an inducer for inducing a mesenchymal stem cell to differentiate into an islet cell.

BACKGROUND ART

Diabetes mellitus (DM) is an endocrine and metabolic disease characterized by disorders of glucose and lipid metabolism. According to forecasts published by the World Health Organization and the International Diabetes Federation, by 2030, there will be 370 million patients with diabetes worldwide. Currently, there are more than 45 million DM patients in China, ranking second only to India. Although their etiologies are different, they are all manifested as defects in the number and function of pancreatic islet cells, and ultimately require treatment with insulin. Although some progress has been made in the use of insulin, especially in the form of insulin formulations and administration routes in recent years, practice has proved that exogenous insulin cannot control blood glucose perfectly and constantly maintain normal blood glucose constant as the human body secretes insulin. Cell replacement therapy is an important method for the treatment of diabetes, which is an effective method closer to the physiological way to achieve continuous monitoring and fine regulation of blood glucose. In recent years, transplantation of islet cells through hepatic portal vein has also achieved some therapeutic effects in treating diabetes, but islet cell transplantation is faced with two problems: insufficient donor sources and severe immune rejection.

Stem cells, as a kind of cells with self-renewal and multi-differentiation, can differentiate into functional islet cells under certain conditions, so they can be used as a new source of islet cells. There are currently three ways to obtain islet cells from stem cell differentiation: 1. embryonic stem cells differentiation; 2. islet stem cells or islet precursor cell differentiation; 3. adult stem cells differentiation. As embryonic stem cells are ethically controversial and it is difficult to obtain islet stem cells, adult stem cells can be used as the source of islet cells due to their wide sources and lack of ethical disputes.

The current methods of stem cell induction mainly include induction in vitro, gene modification, protein transduction and tissue microenvironment induction, wherein induction in vitro is the differentiation of stem cells into target cells by using different stimulating factor combinations. However, different laboratories have different conditions for inducing differentiation, and the mechanism of inducing differentiation is not clear, therefore, the efficiency of inducing differentiation is low, the secretion capacity of islets is only about 1% of normal islets, and the induction process is complicated with long induction time, resulting in small number of cells with low functions.

SUMMARY OF THE INVENTION

The objective of the present invention is to solve the above problems in the prior art and provide an inducer for inducing a mesenchymal stem cell to differentiate into an islet cell, wherein each component is safe and non-toxic, requiring fewer steps and short time to induce differentiation, with high induction efficiency.

To achieve the above objective, the present invention adopts the following technical solution: an inducer for inducing a mesenchymal stem cell to differentiate into an islet cell, wherein the inducer is consisted of the following components: GLP-1, parathyroid hormone, paracetamol, rapamycin, icariin, trametinib, EPO and VEGF.

The mass concentration ratio of each component is as follows: GLP-1 20-40 mg/L, parathyroid hormone 6-12 mg/L, paracetamol 2-8 mg/L, rapamycin 2-8 mg/L, icariin 2-8 mg/L, trametinib 0.3-0.6 mg/L, EPO 2-4 µg/L, VEGF 2-4 µg/L.

Preferably, the mass concentration ratio of each component is as follows: GLP-1 30 mg/L, parathyroid hormone 9 mg/L, paracetamol 5 mg/L, rapamycin 5 mg/L, icariin 5 mg/L, trametinib 0.4 mg/L, EPO 3 µg/L, VEGF 3 µg/L.

The inducer for inducing a mesenchymal stem cell to differentiate into an islet cell provided by the present invention has the following advantages:

1. no need for gene transfection, so there is no genetic modification and cancer risk;
2. fewer induction steps: the methods currently reported in the literature are mainly two-step or three-step methods, and only one step is required to use the inducer of the present invention;
3. short induction time: current literature generally requires more than 10 days for induction, and only 5 days for the inducer of the present invention;
4. the inducer of the invention is used to induce mesenchymal stem cells into islet cells with high differentiation efficiency;
5. all components of the inducer of the present invention are safe and non-toxic;
6. after the induction of the differentiation of mesenchymal stem cells into islet cells, there is no rejection after transplantation and no ethical issues but with high safety, thus it has broad clinical application prospects.

BRIEF DESCRIPTION OF THE DRAWINGS

The sole FIGURE is the reaction of dithizone staining, showing that the induced group of the present invention is red after dithizone staining.

DETAILED DESCRIPTION OF EMBODIMENTS

Example 1

The inducer of this example for inducing a mesenchymal stem cell into an islet cell was consisted of the following components with a mass concentration ratio: GLP-1 30 mg/L, parathyroid hormone 9 mg/L, paracetamol 5 mg/L, rapamycin 5 mg/L, icariin 5 mg/L, trametinib 0.4 mg/L, EPO 3 µg/L, VEGF 3 µg/L. The above components was added to serum-free medium for human mesenchymal stem cells (or DMEM+10% FBS or other commercially available medium for mesenchymal stem cells) in turn according to the mass concentration ratio, followed by mixing well, filtering and sterilizing.

The components of the inducer of the present invention were all commercially available products: serum-free medium for human mesenchymal stem cells, brand LONZA, catalog number 00190632; GLP-1 (glucagon-like peptide 1), brand Sigma, catalog number scp0153; parathyroid hormone, brand Sigma, catalog number P7036; paracetamol, Shanghai Yiji Industrial Co., Ltd., catalog number Y903952;

rapamycin, brand TargetMol, catalog number T1537; icariin, Shanghai Microcrystalline Bio, catalog No. 489-32-7; trametinib, brand Meilun Bio, catalog number MB5401; EPO, brand PeproTech, catalog number CYT-201; VEGF, brand PeproTech, catalog number 96-100-20-2.

Example 2

The inducer of this example for inducing a mesenchymal stem cell into an islet cell was consisted of the following components with a mass concentration ratio: GLP-1 20 mg/L, parathyroid hormone 6 mg/L, paracetamol 2 mg/L, rapamycin 2 mg/L, icariin 2 mg/L, trametinib 0.3 mg/L, EPO 2 μg/L, VEGF 2 μg/L. The above components was added to serum-free medium for human mesenchymal stem cells (or DMEM+10% FBS) in turn according to the mass concentration ratio, followed by mixing well, filtering and sterilizing.

Example 3

The inducer of this example for inducing a mesenchymal stem cell into an islet cell was consisted of the following components with a mass concentration ratio: GLP-1 40 mg/L, parathyroid hormone 12 mg/L, paracetamol 8 mg/L, rapamycin 8 mg/L, icariin 8 mg/L, trametinib 0.6 mg/L, EPO 4 μg/L, VEGF 4 μg/L. The above components was added to serum-free medium for human mesenchymal stem cells (or DMEM+10% FBS) in turn according to the mass concentration ratio, followed by mixing well, filtering and sterilizing.

Example 4

The effect of the inducer was illustrated with human umbilical cord mesenchymal stem cells as an example
I. Induction of Human Umbilical Cord Mesenchymal Stem Cells to Differentiate Into Islet Cells Human umbilical cord mesenchymal stem cells of passage 3 were digested with 0.125%~0.01% Trypsin-EDTA solution for cells collection, to prepare a cell suspension. The density of living cells counted by a cytometer was adjusted to $1 \times 10^4/cm^2$, and cells were inoculated in a 24-well plate with a polylysine-treated sterile cover glass in advance to prepare a cell slide. When cells reached close to 80% confluence, they were induced to differentiate when they grow vigorously, see Table 1 for grouping.

TABLE 1

Induction grouping

| Groups | Induction conditions |
|---|---|
| Control group (blank control) | Serum-free medium for human mesenchymal stem cells. |
| Induction group 1 (conventional method) | Conventional differentiation medium: niacinamide 1.2 g/L, taurine 0.50 g/L, GLP-1 30.5 mg/L; serum-free medium for human mesenchymal stem cells. |
| Induction group 2 (present invention) | The differentiation medium of the present invention in Example 1 |

II. Identification of Islet Cells After Induction (I) Dithizone staining reaction: the islet cells obtained after 5 days of induction in the above three groups (induction group 1 needed to induce differentiation for 10 days) were removed from the original medium, and washed twice with PBS, each with addition of 2 ml PBS and 50 μl dithizone working solution, incubating at 37° C. for 10 min, followed by removal of the staining solution, washing twice with PBS, and then the staining of cells was observed and took pictures The results were shown in the FIGURE. The dithizone staining results in two induction groups were red (as shown in the sole FIGURE) indicating positive reaction, and there was negative reaction in the control group.

(II) Chemiluminescence immunoassay to detect insulin level: the cell culture supernatants of the above three groups 5 days after induction (induction group 1 needed to be induced to differentiate for 10 days) were detected the insulin content. The concentration of insulin secreted by cells in induction group 2 was 518.7 mU/L, which was much higher than the concentration of insulin secreted by cells in induction group 1 of 212.1 mU/L, while the insulin concentration in the blank control group was zero, indicating that the inducer of the present invention could significantly improve the induction efficiency.

(III) Detection of the function of islet cells for the islet-like cells induced by the inducer of the present invention by ELISA kit: This detection procedure directly followed the standard procedure of "C-peptide ELISA assays" provided by Mercodia. In the final result, C-peptide was detected, indicating that the islet-like cells obtained by differentiation induced by the inducer of the present invention could secrete insulin.

(IV) Glucose stimulation test: 100 islet cell clusters (50~150 μm) induced to differentiate for 5 days by the inducer of the present invention were picked into a 1.5 ml centrifuge tube, and washed twice with PBS, with addition of 1 ml sugar-free DMEM to pre-culture for 3-6 h, followed by culturing in 300 μl DMEM containing 5.6 mmol/L glucose and 16.7 mmol/L glucose for 2 h in sequence, and the supernatants were collected. The secretion of insulin under the stimulation of different concentrations of glucose in the supernatant was detected by ELISA. Insulin was almost undetectable in the cell supernatant of the control group, and the induced islet cell group secreted a small amount under stimulation of 5.6 mmol/L glucose, but after 2 h incubation with 16.7 mmol/L glucose, insulin secretion increased significantly ($P<0.001$), which was about twice as high as under low-sugar conditions. The results showed that the cell mass was sensitive to glucose stimulation after induction, and its insulin secretion was regulated by the external environment.

(V) Transplantation in vivo experiment: a diabetic rat model was created firstly. Adult Wistar rats (both sexes) with about 180-200 g weight were selected. Each rat was intraperitoneally injected with streptozotocin at a dose of 70 mg/kg. Streptozotocin powder was prepared into liquid with 0.1 M citric acid buffer (PH=4.5), ready for use freshly. When the blood glucose of the rat rose ($\geq 16.7$ mmol/L) and kept stable for one week, it indicated that the diabete model had been established. Under aseptic conditions, 300 islet-like cell clusters (50-150 μm) induced by the inducer of the present invention were injected into the kidney cyst or small branch of the hepatic portal vein of diabetic rats. After the operation, the blood glucose was observed regularly. Results: The blood glucose of diabetic rats dropped by 7.3 mmol/L on average 3 days after cell implantation. This showed that the islet cell cluster obtained by using the inducer of the present invention to induce differentiation had a significant hypoglycemic effect.

The invention claimed is:
1. An inducer for inducing a human umbilical cord mesenchymal stem cell to differentiate into an islet cell, wherein the inducer is a liquid consisting of the following components: GLP-1, parathyroid hormone, paracetamol, rapamycin, icariin, trametinib, EPO, and VEGF; wherein the mass concentration of each component is as follows: GLP-1 20-40 mg/L, parathyroid hormone 6-12 mg/L, paracetamol 2-8 mg/L, rapamycin 2-8 mg/L, icariin 2-8 mg/L, trametinib 0.3-0.6 mg/L, EPO 2-4 µg/L, and VEGF 2-4 µg/L.

2. The inducer for inducing a mesenchymal stem cell to differentiate into an islet cell according to claim 1, wherein the mass concentration ratio of each component is as follows: GLP-1 30 mg/L, parathyroid hormone 9 mg/L, paracetamol 5 mg/L, rapamycin 5 mg/L, icariin 5 mg/L, trametinib 0.4 mg/mL, EPO 3 µg/L, and VEGF 3 µg/L.

3. A method for preparing an inducer, wherein the inducer is for inducing a human umbilical cord mesenchymal stern cell to differentiate into an islet cell, the method comprising: adding GLP-1 20-40 mg/L, parathyroid hormone 6-12 mg/L, paracetamol 2-8 mg/L, rapamycin 2-8 mg/L, icariin 2-8 mg/L, trametinib 0.3-0.6 mg/L, EPO 2-4 µg/L, and VEGF 2-4 µg/L into a serum-free medium for human mesenchymal stem cells, mixing the medium, filtering the medium, and sterilizing the medium to obtain the inducer.

\* \* \* \* \*